United States Patent
Jin et al.

(10) Patent No.: US 8,542,793 B1
(45) Date of Patent: Sep. 24, 2013

(54) SYSTEM FOR MEASURING SAMPLE PORE USING COMPUTED TOMOGRAPHY AND STANDARD SAMPLE AND METHOD THEREOF

(75) Inventors: Jae Hwa Jin, Daejeon (KR); Jun Ho Kim, Jeonnam (KR); Min Jun Kim, Daejeon (KR)

(73) Assignee: Korea Institute of Geoscience and Mineral Resources (KIGAM), Daejeon (KR)

( * ) Notice: Subject to any disclaimer, the term of this patent is extended or adjusted under 35 U.S.C. 154(b) by 0 days.

(21) Appl. No.: 13/989,141

(22) PCT Filed: Sep. 30, 2011

(86) PCT No.: PCT/KR2011/007269
§ 371 (c)(1),
(2), (4) Date: May 23, 2013

(87) PCT Pub. No.: WO2012/141392
PCT Pub. Date: Oct. 18, 2012

(30) Foreign Application Priority Data

Apr. 13, 2011 (KR) .................. 10-2011-0034399

(51) Int. Cl.
*G01B 15/02* (2006.01)
*G01N 23/06* (2006.01)

(52) U.S. Cl.
USPC .................................. 378/54; 378/4; 378/56

(58) Field of Classification Search
USPC ..................... 378/4, 10, 54, 56–58
See application file for complete search history.

(56) References Cited

U.S. PATENT DOCUMENTS

| | | | | |
|---|---|---|---|---|
| 5,036,193 A * | 7/1991 | Davis et al. | .................... | 250/255 |
| 5,359,194 A | 10/1994 | Moss | | |
| 5,430,291 A | 7/1995 | Pepin et al. | | |
| 7,564,944 B2 * | 7/2009 | Kato | ............................... | 378/58 |
| 7,714,304 B2 | 5/2010 | Poglitsch et al. | | |
| 7,853,045 B2 | 12/2010 | Touati et al. | | |
| 8,081,796 B2 * | 12/2011 | Derzhi et al. | ................. | 382/100 |
| 2008/0217559 A1 | 9/2008 | Poglitsch et al. | | |
| 2009/0110242 A1 | 4/2009 | Touati et al. | | |
| 2010/0128933 A1 | 5/2010 | Derzhi et al. | | |

FOREIGN PATENT DOCUMENTS

| | | | |
|---|---|---|---|
| JP | 2003-240527 A | 8/2003 | |
| JP | 2006-084483 A | 3/2006 | |
| JP | 2009-505083 A | 2/2009 | |
| KR | 10-2011-0054092 A | 5/2011 | |
| WO | WO 2009/058390 A1 | 5/2009 | |

* cited by examiner

*Primary Examiner* — Thomas R Artman
(74) *Attorney, Agent, or Firm* — Rabin & Berdo, P.C.

(57) ABSTRACT

The present invention relates to a system for measuring a sample pore using a computed tomography (CT) and a standard sample and to a method thereof, more particularly to a system for measuring a sample pore using a computed tomography (CT) and a standard sample and to a method thereof, wherein the number of pixels in the count range of a cross-sectional image of the measurement sample and the number of pixels corresponding to the gray level range of the pore are calculated with reference to the count range utilized in the cross-sectional image of the standard sample and the gray level range of the pore so as to accurately measure the porosity of the measurement sample after performing a CT scan of the standard sample and the measurement sample together using a CT scanner.

9 Claims, 11 Drawing Sheets

SYSTEM FOR MEASURING SAMPLE PORE USING COMPUTED TOMOGRAPHY AND STANDARD SAMPLE AND METHOD THEREOF

TECHNICAL FIELD

The present invention relates to a system for measuring a sample pore using a computed tomography (CT) and a standard sample and to a method thereof, more particularly to a system for measuring a sample pore using a computed tomography (CT) and a standard sample and to a method thereof, wherein the number of pixels in the count range of a cross-sectional image of the measurement sample and the number of pixels corresponding to the gray level range of the pore are calculated with reference to the count range utilized in the cross-sectional image of the standard sample and the gray level range of the pore so as to accurately measure the porosity of the measurement sample after performing a CT scan of the standard sample and the measurement sample together using a CT scanner.

BACKGROUND ART

In general computed tomography apparatus (CT) for medical purposes shown in FIG. 1, a CT beam, which is transmitted by CT beam transmittance part 10, passes through an object 30 and signals passing through the object are detected by a detector, so that the object is restored as three-dimensional images by using the signals to output them to an user.

In case of the above manner, since the three-dimensionally restored object is randomly cut and only the cut planar images are checked, it cannot effectively calculate of the volume of a specific part existed in the inside of the photographed object.

The CT is widely used in medical. Also, it is widely used to diagnose the internal structure of the human body. Moreover, the utilization thereof for observing the defective parts such as the internal structure of the product, the internal inclusions or internal cracks in the field of industrial has been increased.

In particular, recently, it has begun to introduce the CT in the field of the geological resource. One of its main purposes is to observe the internal characteristics of the samples obtained from the strata.

Any gap generated from the crack of the strata or the gap between the particles of constituting the strata which is called as a pore.

Since the useful substances such as oil, gas, and groundwater can be flowed smoothly through these pores in the stratum, it is important to identify quantitatively the amount of the pores in the strata through the analysis of samples obtained from the strata.

The amount of the pores in the strata is mainly expressed as a population parameter called as a porosity, which is represented by the following formula.

Porosity(%)=the amount of the pores of sample/total volume of the sample*100 (formula)

There are an immersion process, a gas process, and a mercury process etc. in a method for measuring the pores from geological samples. In the above methods, a water, a gas, and a mercury are filled into or discharged out the sample or discharged to measure the quantity of demand.

In these methods, accessory materials such as water, helium gas, mercury etc. are required and appropriate instrument should be utilized. Also, it takes a considerable amount of time to measure the sampling unit. Accordingly, it is necessary to save the time and expense. Also, the necessity of developing accurate measuring method of the porosity has been brought up.

There are continuous attempts for observing the internal structure of any particular substance using the CT. Recently, there is an attempt for identifying and quantifying the volume of specific substances in the strata sample.

That is, there is an attempt for easily measuring the porosity thereof by analyzing the strata sample through the CT. However, a highly reliable method for measuring the porosity has not been presented yet.

Where the porosity is measured through the CT analysis, the numerical values read in sectional image of the CT image are variable.

If the sample of the geological resource having the same property is collected in the same strata, as though the CT scan on it is progressed in the transceiving conditions of the CT beam, in case of different sizes thereof, the gray level values of representing the pores of the sample can be only different from each other.

Also, in case of representative samples of the geological resource, the groundwater, the oil, or the gas is filled in the pores. However, the gray level values of representing the pores of the sample in the CT sectional image can be only different according to the kind of the filling material of the pore.

By scanning the standard sample and the sample to be measured (hereinafter, referred to as the measurement sample is defined) together by means of the CT, a system for accurately measuring the porosity of the measurement sample using the numerical values read from the sectional images of the standard sample has been demanded.

DISCLOSURE

Technical Problem

Therefore, the present invention has been made in view of the above-mentioned problems, and an object of the present invention is to provide a system for measuring a sample pore using a computed tomography (CT) and a standard sample and to a method thereof in that a tomographic method is simultaneously applied to a standard sample and a measurement sample, thereby reliably measuring the porosity of the measurement sample.

Another object of the present invention is to provide a system for measuring a sample pore using a computed tomography (CT) and a standard sample and to a method thereof in that the amount of the area of a gap generated from the crack of the strata or between particles of constituting the sample can be effectively calculated from one sectional image of the CT image of the sample through an easy computer equation and the same computer equation is applied to the contiguous sectional images, so that it can find the porosity existed in the predetermined volume of the sample.

Further another object of the present invention is to provide a system for measuring a sample pore using a computed tomography (CT) and a standard sample and to a method thereof in that the numerical data read from the sectional image of the standard sample is utilized, thereby remarkably enhancing the accuracy and precision of the measurement of the porosity of the measurement sample.

Technical Solution

In accordance with the present invention to achieve the object thereof, there is provided a system for measuring a sample pore using a computed tomography (CT) and a standard sample comprising:

a main body 700 having a CT beam transmission part 100, a detector 200, and a sample rotating device 310;

the CT beam transmission part 100 installed and constructed in a first supporting member 710 installed in one side of the main body so as to transmit a CT beam;

the detector 200 installed and constructed in a second supporting member 720 installed in the other side of the main body so as to acquire the CT beam transmitted through the CT beam transmission part 100;

the sample rotating device 310 installed and constructed between the CT beam transmission part 100 and the detector 200 and rotating a standard sample and the measurement sample;

a sample rotating motor 420 for rotating the sample rotating device installed and constructed in the inside of the main body; and a central control means 500 for transmitting operation signals to the sample rotating motor 420, transmitting a CT beam transmission signal to the CT beam transmission unit, acquiring sectional images of the standard sample and the measurement sample analyzed by the detector 200, acquiring a count range and a gray level range of a pore from the sectional image of the standard sample, and calculating the number of pixels in the count range of the sectional image of the measurement sample and the number of pixels corresponding to the gray level range of the pore with reference to the count range utilized in the sectional image of the standard sample and the gray level range of the corresponding pore so as to measure the porosity of the measurement sample.

Advantageous Effects

According to the system for measuring the sample pore using the computed tomography (CT) and the standard sample and to the method thereof, there is an effect in that the sectional images on the standard sample and the measurement sample are acquired by using the computed tomography (CT) and the gray level range of the pore is acquired from the sectional images of the standard sample, and then, the corresponding range can be applied to the measurement sample, thereby reliably measuring the porosity of the measurement sample.

According to the method of measuring the porosity of the present invention, if the intervals of the adjacent cross-sectional images are infinitely narrow, since the porosity can be derived very accurately in theory, it can be expected that two porosity values of the standard and measurement samples are identical with each other within the error range.

Especially, according to the system for measuring the sample pore using the computed tomography (CT) and the standard sample and to the method thereof, it takes a short time to scan the CT image and measure the porosity in comparison with the conventional immersion process, gas process, and mercury process etc., thereby expecting the reliable porosity and treating various samples.

BRIEF DESCRIPTION OF THE DRAWINGS

The foregoing and other objects, features and advantages of the present invention will become more apparent from the following detailed description when taken in conjunction with the accompanying drawings in which.

DESCRIPTIONS ON REFERENCE NUMBERS FOR THE MAJOR COMPONENTS IN THE DRAWINGS

Figure 1:
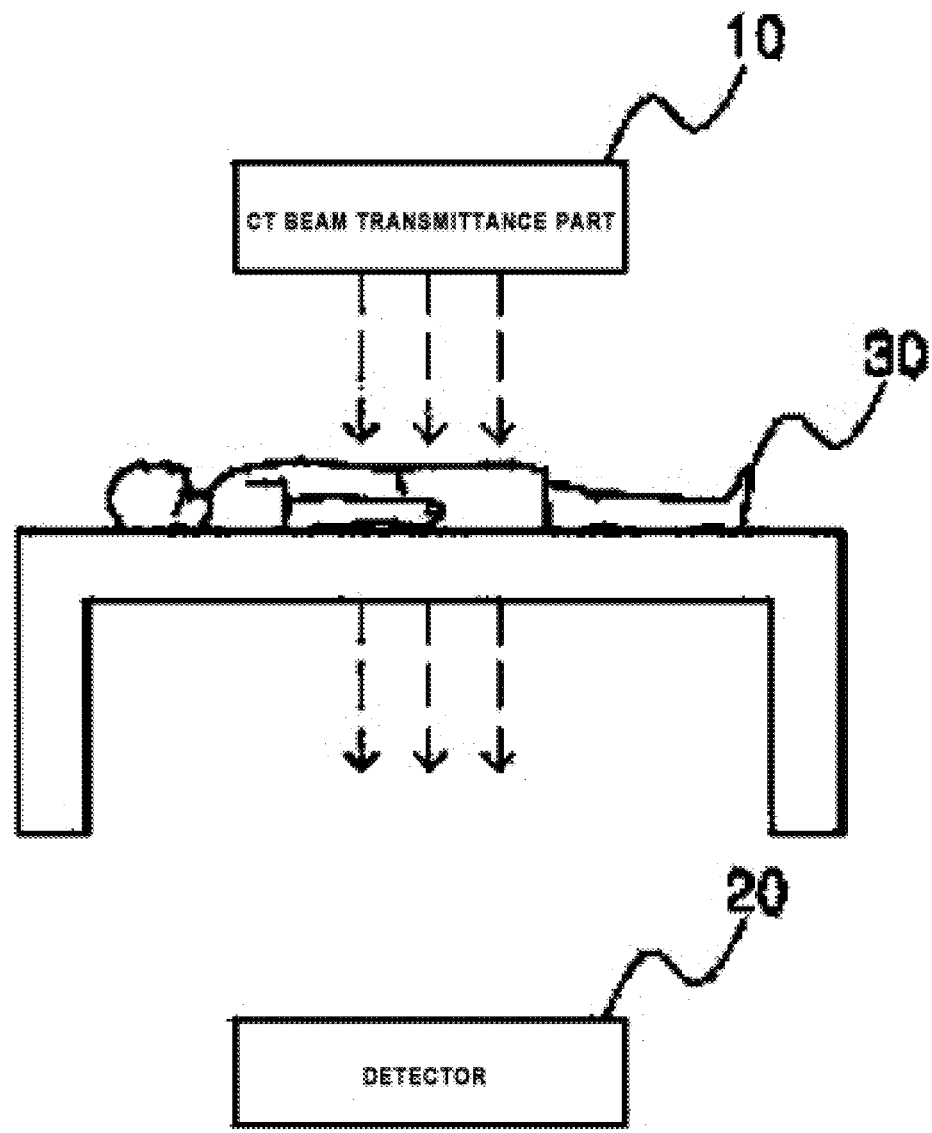
FIG. 1 is an example view illustrating a conventional computed tomography apparatus.

100: CT beam transmission unit
200: detector

310: sample rotating device
420: sample rotating motor
500: central control means
700: main body

BEST MODE

Mode for Invention

Hereinafter, exemplary embodiments of the present invention will be described in detail with reference to the accompanying drawings.

In accordance with the present invention to achieve the object thereof, there is provided a system for measuring a sample pore using a computed tomography (CT) and a standard sample comprising:

a main body 700 having a CT beam transmission part 100, a detector 200, and a sample rotating device 310;

the CT beam transmission part 100 installed and constructed in a first supporting member 710 installed in one side of the main body so as to transmit a CT beam;

the detector 200 installed and constructed in a second supporting member 720 installed in the other side of the main body so as to acquire the CT beam transmitted through the CT beam transmission part 100;

the sample rotating device 310 installed and constructed between the CT beam transmission part 100 and the detector 200 and rotating a standard sample and the measurement sample;

a sample rotating motor 420 for rotating the sample rotating device installed and constructed in the inside of the main body; and a central control means 500 for transmitting operation signals to the sample rotating motor 420, transmitting a CT beam transmission signal to the CT beam transmission unit, acquiring sectional images of the standard sample and the measurement sample analyzed by the detector 200, acquiring a count range and a gray level range of a pore from the sectional image of the standard sample, and calculating the number of pixels in the count range of the sectional image of the measurement sample and the number of pixels corresponding to the gray level range of the pore with reference to the count range utilized in the sectional image of the standard sample and the gray level range of the corresponding pore so as to measure the porosity of the measurement sample.

In the meantime, according to another embodiment of the present invention, a system for measuring a sample pore using a computed tomography (CT) and a standard sample having a main body 700 having a CT beam transmission part 100, a detector 200, and a sample rotating device 310; the CT beam transmission part 100 installed and constructed in a first supporting member 710 installed in one side of the main body so as to transmit a CT beam; and the detector 200 installed and constructed in a second supporting member 720 installed in the other side of the main body so as to acquire the CT beam transmitted through the CT beam transmission part 100 includes:

the sample rotating device 310 installed and constructed between the CT beam transmission part 100 and the detector 200 in the main body and rotating a standard sample and the measurement sample;

a sample rotating motor 420 for rotating the sample rotating device installed and constructed in the inside of the main body; and a central control means 500 for transmitting operation signals to the sample rotating motor 420, transmitting a CT beam transmission signal to the CT beam transmission unit, acquiring sectional images of the standard sample and the measurement sample analyzed by the detector 200, acquiring a count range and a gray level range of a pore from the sectional image of the standard sample, and calculating the number of pixels in the count range of the sectional image of the measurement sample and the number of pixels corresponding to the gray level range of the pore with reference to the count range utilized in the sectional image of the standard sample and the gray level range of the corresponding pore so as to measure the porosity of the measurement sample.

Here, the sample rotating device 310 includes a sample holder 320 installed and constructed on an upper part thereof, and a receiving part 330 coupled to the sample holder 320 and having an inner space for receiving the standard sample 300a and the measurement sample 300b therein.

Here, the sample rotating device 310 includes:

a sample holder 320 installed and constructed on an upper part thereof; and a receiving part 330 coupled to the sample holder 320 and having a lower chamber 331 for accommodating any one of the standard sample 300a and the measurement sample 300b, an upper chamber 332 for accommodating the other sample of the standard sample 300a and the measurement sample 300b, which is not accommodated in the lower chamber, and a separation membrane 330a for separating the upper part and the lower part formed between the lower chamber and the upper chamber.

Here, in the receiving part 330, an inner diameter of a space of accommodating the standard sample is larger than that of a space of accommodating the standard sample.

Here, the central control means 500 includes:

an operation signal transmission unit 510 for transmitting the operation signals to the sample rotating motor 420 and transmitting the CT beam transmission signal to the CT beam transmission unit;

an image acquisition unit 520 for acquiring the sectional images of the standard sample and the measurement sample analyzed by the detector 200;

an image storage unit 530 for storing the sectional images acquired by the image acquisition unit 520;

a count range acquisition unit 540 for acquiring the count range so as to measure the pores of the standard sample and the measurement sample;

a pore gray level range acquisition unit 550 for acquiring the pore gray level range of a specific portion in the sectional images of the standard sample and the measurement sample;

an unit for counting the number of pore pixels 560 for receiving the count range acquired by the count range acquisition unit 540 and the pore gray level range acquired by the pore gray level range acquisition unit 550 and counting the number of pixels corresponding to the pore gray level range within the count range of the sectional images of the standard sample and the measurement sample;

a porosity calculation unit 570 for calculating the porosity with reference to the number of pixels corresponding to the pore gray level range counted by the unit for counting the number of pore pixels 560 and the number of the pixels within the count range;

an unit for managing the progress of the measurement sample 580 for receiving the count range acquired through the count range acquisition unit 540 and the pore gray level range acquired through the pore gray level range acquisition unit 550 so as to calculate the porosity from the sectional images of the standard sample acquired by the image acquisition unit 520, again transmitting the acquired count range and pore gray level range to the count range acquisition unit 540 and the pore gray level range acquisition unit 550 so as to calculate the porosity from the sectional images of the measurement sample acquired by the image acquisition unit 520, and again transmitting the counted number of the pixels to the porosity calculation unit 570 by transmitting the count signal to the unit for counting the number of pore pixels 560 so as to count the number of the pixels, thereby calculating the porosity thereof; and the central control unit 590 for controlling a signal flow between each unit.

Here, the central control means 500 according to another aspect of the present invention including:

an operation signal transmission unit 510 for transmitting the operation signals to the sample rotating motor 420 and transmitting the CT beam transmission signal to the CT beam transmission unit;

an image acquisition unit 520 for acquiring the sectional images of the standard sample and the measurement sample analyzed by the detector 200;

an image storage unit 530 for storing the sectional images acquired by the image acquisition unit 520;

a count range acquisition unit 540 for acquiring the count range so as to measure the pores of the standard sample and the measurement sample;

a pore gray level range acquisition unit 550 for acquiring the pore gray level range of a specific portion in the sectional images of the standard sample and the measurement sample;

an unit for counting the number of pore pixels 560 for receiving the count range acquired by the count range acquisition unit 540 and the pore gray level range acquired by the pore gray level range acquisition unit 550 and counting the number of pixels corresponding to the pore gray level range within the count range of the sectional images of the standard sample and the measurement sample;

a porosity calculation unit 570 for calculating the porosity with reference to the number of pixels corresponding to the pore gray level range counted by the unit for counting the number of pore pixels 560 and the number of the pixels within the count range;

an unit for managing the progress of the measurement sample 580 for receiving the count range acquired through the count range acquisition unit 540 and the pore gray level range acquired through the pore gray level range acquisition unit 550 so as to calculate the porosity from the sectional images of the standard sample acquired by the image acquisition unit 520, again transmitting the acquired count range and pore gray level range to the count range acquisition unit 540 and the pore gray level range acquisition unit 550 so as to calculate the porosity from the sectional images of the measurement sample acquired by the image acquisition unit 520, and again transmitting the counted number of the pixels to the porosity calculation unit 570 by transmitting the count signal to the unit for counting the number of pore pixels 560 so as to count the number of the pixels, thereby calculating the porosity thereof;

an unit 595 for storing the porosity of the previous standard sample for storing a pore gray level range and a porosity of the standard sample calculated in advance;

a gray level recalculation unit 596 for generating a recalculation signal so as to recalculate the pore gray level range where the difference between the porosity of the standard sample calculated by the porosity calculation unit 570 and the porosity of the standard sample pre-stored in the unit 595 for storing the porosity of the previous standard sample is not within the error range thereof; and the central control unit 590 for controlling a signal flow between each unit.

Here, the central control means 500 serves to calculate the number of pixels in the count range, calculate the number of pixels corresponding to the gray level range, and calculate the porosities per each sectional image with reference to the calculated number of pixels.

Here, the porosity of the standard sample stored in the unit 595 for storing the porosity of the previous standard sample is calculated in advance through an immersion process, a gas process, and a mercury process.

Here, the ingredients of the standard sample are identical with those of the measurement sample.

In the meantime, a method for measuring a sample pore using a computed tomography (CT) and a standard sample according to one embodiment of the present invention comprises:

an operation signal transmitting step S100 of transmitting operation signals to a sample rotating motor 420 by means of an operation signal transmission unit 510 to rotate a sample rotating device 310 and transmitting a CT beam transmission signal to a CT beam transmission unit;

a sectional image acquiring step S200 of acquiring sectional images of a standard sample and a measurement sample analyzed by a detector 200 by means of an image acquisition unit 520;

a sectional image storing step S300 of storing the sectional images acquired by the image acquisition unit 520 in an image storage unit 530; and a measurement sample porosity calculating step S400 of acquiring a count range and a gray level range of a pore from the sectional images of the standard sample, which are stored in the image storage unit 530, by means of a central control means and calculating the number of pixels in the count range of the sectional image of the measurement sample and the number of pixels corresponding to the gray level range of the pore with reference to the count range of the sectional images and the gray level range of the corresponding pore by means of the central control means so as to measure the porosity of the measurement sample.

Meanwhile, a method for measuring a sample pore using a computed tomography (CT) and a standard sample according to another embodiment of the present invention comprises:

an operation signal transmitting step S100 of transmitting operation signals to a sample rotating motor 420 by means of an operation signal transmission unit 510 to rotate a sample rotating device 310 and transmitting a CT beam transmission signal to a CT beam transmission unit;

a sectional image acquiring step S200 of acquiring sectional images of a standard sample and a measurement sample analyzed by a detector 200 by means of an image acquisition unit 520;

a sectional image storing step S300 of storing the sectional images acquired by the image acquisition unit 520 in an image storage unit 530;

a measurement sample porosity calculating step S400 of acquiring a count range and a gray level range of a pore from the sectional images of the standard sample, which are stored in the image storage unit 530, by means of a central control means and calculating the number of pixels in the count range of the sectional image of the measurement sample and the number of pixels corresponding to the gray level range of the pore with reference to the count range of the sectional images and the gray level range of the corresponding pore by means of the central control means so as to measure the porosity of the measurement sample; and a gray level recalculating step S500 of generating a recalculation signal so as to recalculate the pore gray level range in the central control means, where the difference between the porosity of the standard sample calculated by the central control means and the porosity of the standard sample pre-stored in an unit 595 for storing the porosity of the previous standard sample is not within the error range thereof.

Here, the measurement sample porosity calculating step S400 includes:

a count range acquiring step 410 of acquiring the count range so as to measure the pores of the standard sample by means of a count range acquisition unit 540;

a pore gray level range acquiring step S420 of acquiring the pore gray level range of a specific portion in the sectional images of the standard sample by means of the pore gray level range acquisition unit 550;

a counting step S430 of the number of a standard sample pore pixel of receiving the count range acquired by the count range acquisition unit 540 and the pore gray level range acquired by the pore gray level range acquisition unit 550 in an unit 560 for counting the number of pore pixels and counting the number of pixels corresponding to the pore gray level range within the count range of the sectional images of the standard sample by means of the unit 560 for counting the number of pore pixels;

a standard sample porosity calculating step S440 of calculating the porosity of the standard sample with reference to the number of pixels corresponding to the pore gray level range counted by the unit 560 for counting the number of pore pixels and the number of the pixels within the count range by means of a porosity calculation unit 570; and a measurement sample porosity calculating step S450 of receiving the count range acquired through the count range acquisition unit 540 and the pore gray level range acquired through the pore gray level range acquisition unit 550 so as to calculate the porosity from the sectional images of the standard sample acquired by the image acquisition unit 520, again transmitting the acquired count range and pore gray level range to the count range acquisition unit 540 and the pore gray level range acquisition unit 550 so as to calculate the porosity from the sectional images of the measurement sample, and again transmitting the counted number of the pixels to the porosity calculation unit 570 by transmitting the count signal to the unit 560 for counting the number of pore pixels so as to count the number of the pixels, thereby calculating the porosity of the measurement sample by means of an unit 580 for managing the progress of the measurement sample.

Here, the central control means 500 serves to calculate the number of pixels in the count range, calculate the number of pixels corresponding to the gray level range, and calculate the porosities per each sectional image with reference to the calculated number of pixels.

Here, the porosity of the standard sample stored in the unit 595 for storing the porosity of the previous standard sample is calculated in advance through an immersion process, a gas process, and a mercury process.

Here, the ingredients of the standard sample are identical with those of the measurement sample.

Figure 2:
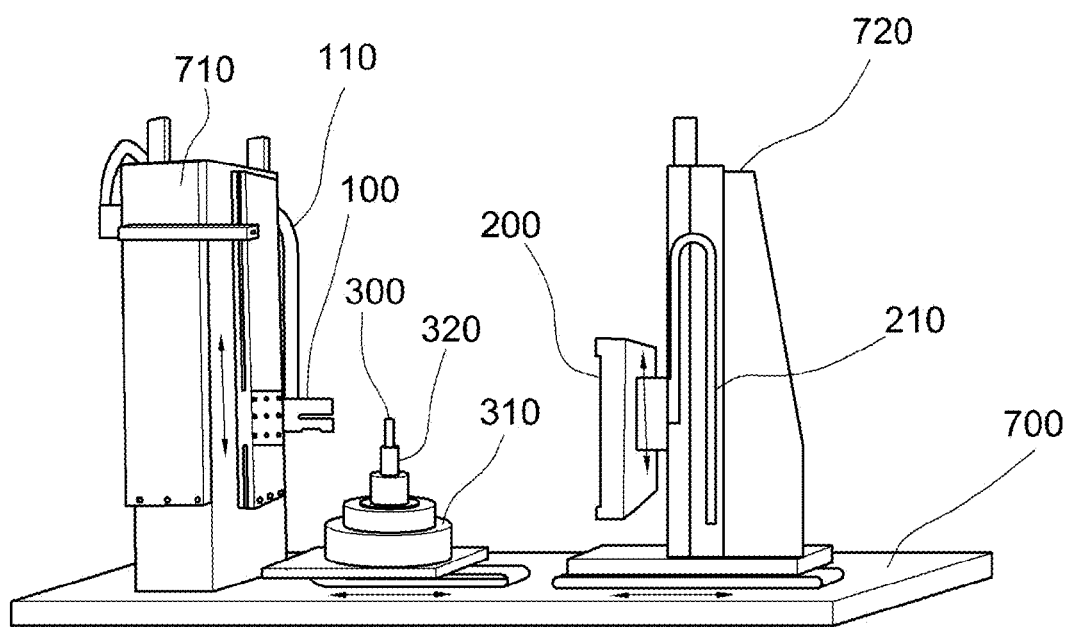
FIG. 2 is a simple constructional view illustrating a main body of a system for measuring a sample pore using a computed tomography (CT) and a standard sample according to one embodiment of the present invention.

FIG. 2 is a simple constructional view illustrating a main body of a system for measuring a sample pore using a computed tomography (CT) and a standard sample according to one embodiment of the present invention.

Figure 3:
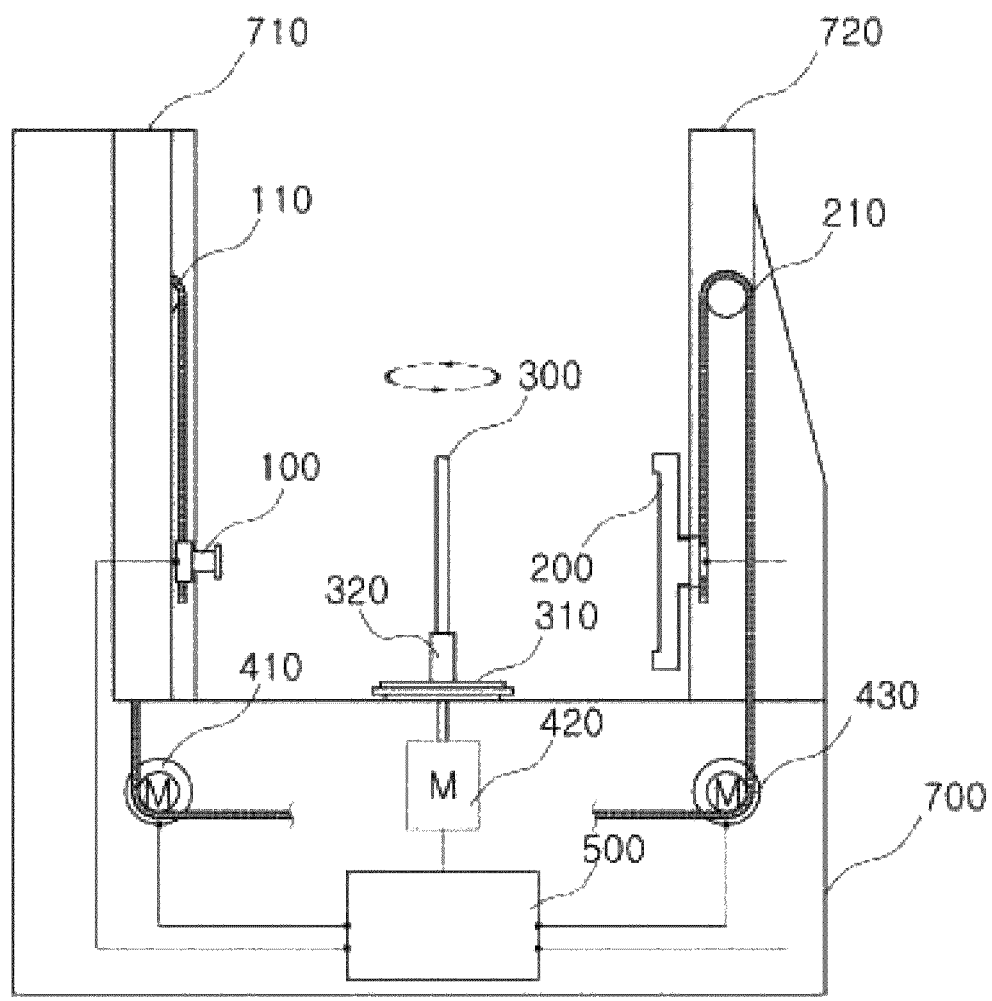
FIG. 3 is a sectional view illustrating a main body of a system for measuring a sample pore using a computed tomography (CT) and a standard sample according to one embodiment of the present invention.

FIG. 3 is a sectional view illustrating a main body of a system for measuring a sample pore using a computed tomography (CT) and a standard sample according to one embodiment of the present invention.

In the case of the conventional medical CT, it performs the CT (computed tomography) scan through the rotation of the CT beam transmission unit 10 and the detector 20. However, in case of the present invention, it rotates the sample of the geological resource. Accordingly, as shown in FIG. 2 and FIG. 3, the system of the present invention includes a main body 700 having a CT beam transmission part 100, a detector 200, and a sample rotating device 310.

At this time, the CT beam transmission part 100 is installed and constructed in a first supporting member 710 installed in one side of the main body 700, so that it serves to transmit a CT beam. Also, the detector 200 is installed and constructed in a second supporting member 720 installed in the other side of the main body 700, so that it serves to acquire the CT beam transmitted through the CT beam transmission part 100.

Here, the sample rotating device 310 is installed and constructed between the CT beam transmission part 100 and the detector 200, so that it serves to rotate a standard sample and a measurement sample.

In order to rotate the sample rotating device in the main body, a sample rotating motor 420 is installed and constructed in the inside of the main body.

To illustrate the operation process thereof, the CT beam transmitted through the CT beam transmission part 100 passes through the sample of the geological resource as a target to be detected in the detector, thereby outputting it to a user.

As one of the key of the present invention, because the sample is rotated, the images can be detected at various angles so as to measure the pore existed in the sample, thereby more accurately measuring the pore and the porosity thereof.

In the meantime, the system for measuring the sample pore using the computed tomography (CT) and the standard sample according to one embodiment of the present invention can include:

the CT beam transmission part 100 installed and constructed in a first supporting member 710 installed in one side of the main body, connected to a CT beam transmission part moving member 110, moved up and down when the CT beam transmission part moving member is moved up and down, and transmitting a CT beam;

the detector 200 installed and constructed in a second supporting member 720 installed in the other side of the main body, connected to a detector moving member 210, moved up and down though the detector moving member 210, and acquiring the CT beam transmitted through the CT beam transmission part 100;

a CT beam transmission part operating motor 410 for moving the CT beam transmission part moving member 110 up and down; and a detector operating motor 430 for moving the detector moving member 210 up and down.

At this time, a central control means serves to transmit operation signals to the CT beam transmission part operating motor 410, the detector operating motor 430 and the sample rotating motor 420, transmit a CT beam transmission signal to the CT beam transmission part 100, and allow the CT beam transmission part 100 and the detector 200 to be simultaneously moved up and down by transmitting an operation signal, which is synchronized with the operation signal of the CT beam transmission part operating motor 410, to the detector operating motor 430.

Also, the system of the present invention can further include an operating part for moving the CT beam transmission part and the detector up and down, rotating the sample rotating device, and allowing the operation of transmitting the CT beam to be selected by the user and a display part for displaying the data detected by the detector.

Figure 4:
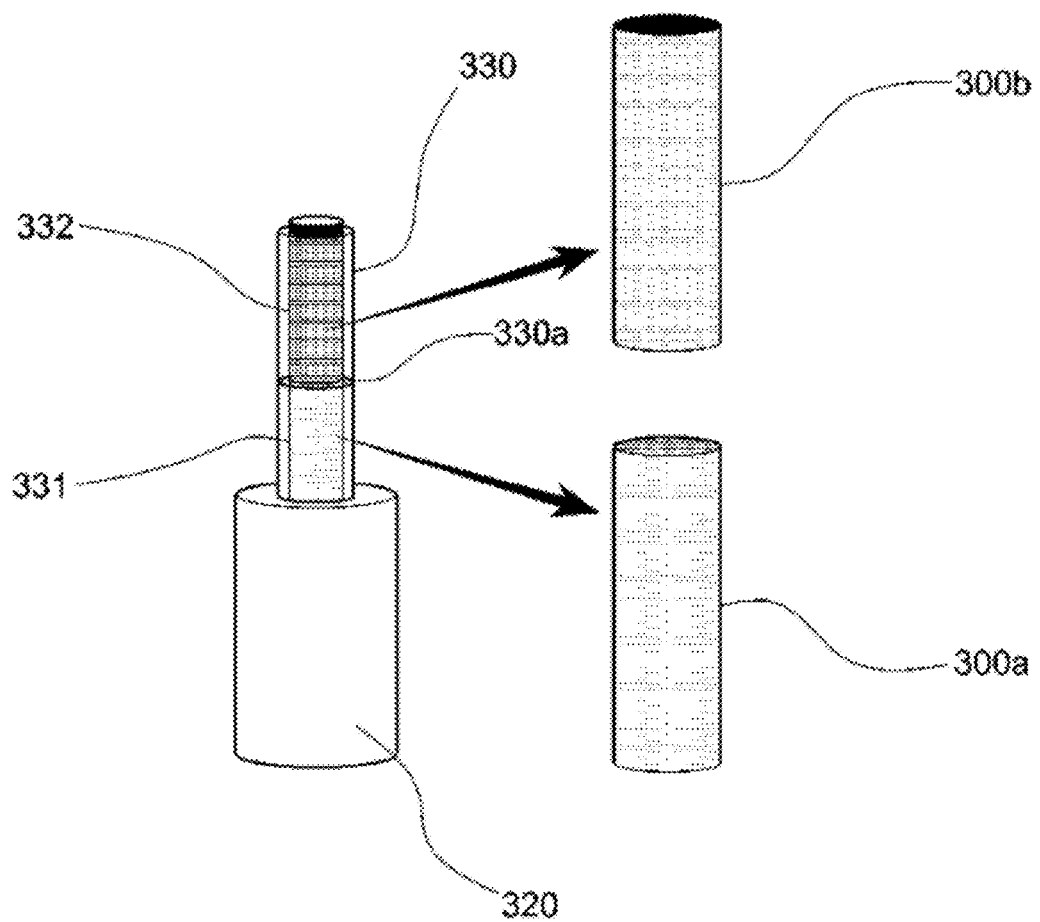
FIG. 4 is a simple example view illustrating a sample holder and a receiving part of a system for measuring a sample pore using a computed tomography (CT) and a standard sample according to one embodiment of the present invention.

FIG. 4 is a simple example view illustrating a sample holder and a receiving part of a system for measuring a sample pore using a computed tomography (CT) and a standard sample according to one embodiment of the present invention.

As shown in FIG. 4, the sample rotating device 310 includes a sample holder 320 installed and constructed on an upper part thereof, and a receiving part 330 coupled to the sample holder 320 and having an inner space for receiving the standard sample 300a and the measurement sample 300b therein.

More concretely, the sample rotating device 310 includes:

the sample holder 320 installed and constructed on an upper part thereof; and the receiving part 330 coupled to the sample holder 320 and having a lower chamber 331 for accommodating any one of the standard sample 300a and the measurement sample 300b, an upper chamber 332 for accommodating the other sample of the standard sample 300a and the measurement sample 300b, which is not accommodated in the lower chamber 331, and a separation membrane 330a for separating the upper part and the lower part formed between the lower chamber 331 and the upper chamber 321.

The receiving part 330 is installed and constructed on the sample holder 320. Preferably, the receiving part 33 is a cylindrical form. The cylindrical receiving part is divided into the upper part and the lower part by means of the separation membrane 330a.

The receiving part 330 includes the upper chamber 332 formed at the upper part thereof and the lower chamber 331 formed at the lower part thereof.

At this time, preferably, the measurement sample 300b is accommodated in the upper chamber 332 and the standard sample 300a is accommodated in the lower chamber 331. However, in some cases, the measurement sample and the standard sample may be placed in reverse.

As shown in FIG. 4, the ingredients of the standard sample are similar to those of the measurement sample. The porosity of the standard sample is already measured and known through an immersion process, a gas process, and a mercury process etc.

Where liquids or gases other than an air is filled in the pore of measurement sample and the ingredients thereof are already known, the same liquids or gases can be filed in the pore of the standard sample.

It is preferred that the diameters and the outer wall thicknesses of the upper the chamber and the lower chamber of the sample holder for accommodating the measurement sample and the standard sample depend on the size of the measurement sample and the thickness of the chamber of accommodating the standard sample.

That is, as shown in FIG. 4, where the measurement sample 300b is accommodated in the upper chamber 332 of the cylindrical sample holder and the standard sample 300a is accommodated in the lower chamber 331, the inner diameter of the lower chamber is slightly larger than that of the upper chamber in view of the thickness of the reservoir of the accommodated standard sample. After all, it is preferred that the outer wall thickness of the lower chamber having the standard sample is matched with that of the upper chamber. That is, the standard sample and the measurement sample are scanned under similar conditions as possible, so that the gray level range of the pore set in the standard sample can be smoothly applied to the measurement sample.

Figure 5:
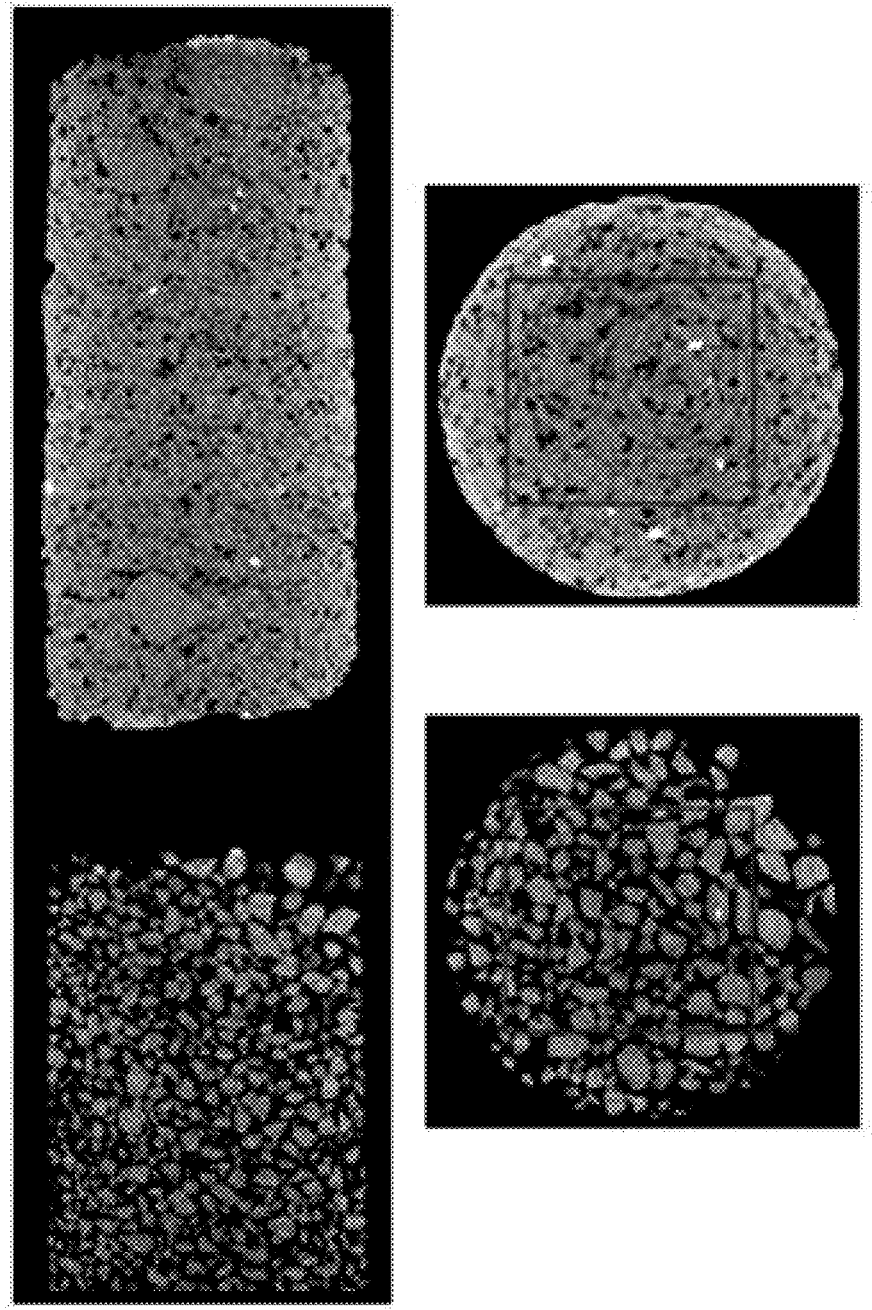
FIG. 5 is an example view illustrating a vertically sectional image of scanned standard and measurement samples and a count range for calculating the pore on a horizontally sectional image by means of a system for measuring a sample pore using a computed tomography (CT) and a standard sample according to one embodiment of the present invention.

FIG. 5 is an example view illustrating a vertically sectional image of scanned standard and measurement samples and a count range for calculating the pore on a horizontally sectional image of a system for measuring a sample pore using a computed tomography (CT) and a standard sample according to one embodiment of the present invention.

Figure 6:
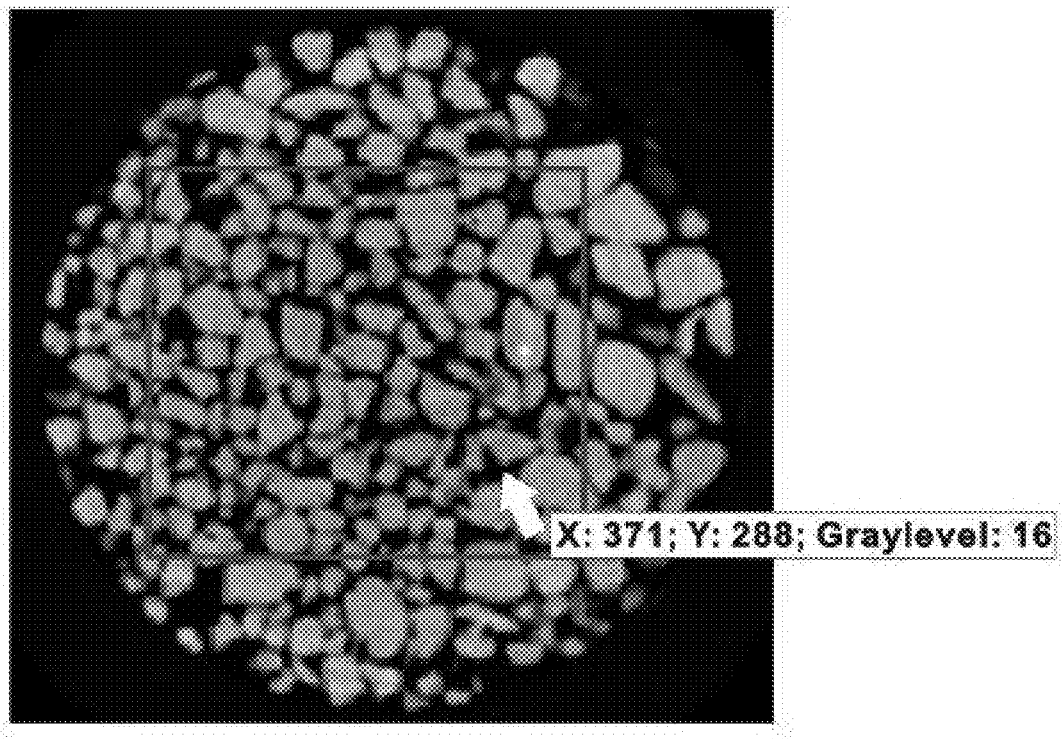
FIG. 6 is an example view illustrating an example of acquiring a gray level on the corresponding region in a case of designating a specific region of a sectional image of scanned standard and measurement samples by means of a system for measuring a sample pore using a computed tomography (CT) and a standard sample according to one embodiment of the present invention.

FIG. 6 is an example view illustrating an example of acquiring a gray level on the corresponding region in a case of designating a specific region of a sectional image of scanned standard and measurement samples of a system for measuring a sample pore using a computed tomography (CT) and a standard sample according to one embodiment of the present invention.

In the manner described with reference to FIG. 4, when the standard sample and the measurement sample are inserted into the sample holder to perform the computed tomography, as shown in FIG. 5, the sectional images of the standard and measurement samples can be secured under the same scan conditions.

As shown in FIG. 5, the upper part of the vertical and the horizontal cross-sectional image is the measurement sample and the lower part of the vertical and horizontal cross-section image is the standard samples.

Each sectional image of the standard sample and the measurement sample is already derived by the computed tomography. Also, since each pixel of constituting each sectional image has an unique gray level information, as shown in FIG. 6, the corresponding gray level value and the positioning value on the specific region of the sectional image can be grasped.

Especially, in the case of the standard sample, since the gap portion between the particles of constituting the sample can be clearly recognized, the gray level range illustrating the pore in the corresponding sectional image can be easily grasped.

In other words, where the range of the gray level corresponding to the pore is determined from the standard sample, the gray level range of the corresponding pore can be utilized as the value of the gray level range of identifying the pore in the measurement sample image as it is.

FIG. 5 illustrates the standard sample acquired by the count range acquisition unit or an example of setting the calculating range of the pore in the sectional image of the measurement sample. It is well shown in the right horizontal cross-section image.

When it sets the range of calculating the pore in each sectional image, the outermost regions should be excluded from the calculation as possible.

That is, after the counter range is set in the sectional images, since it is convenient to apply the counter range to the consecutively contiguous cross-sectional images as it is, the count range set in the first cross-sectional image should not be got out of the following sectional images.

As shown in FIG. 6, where the count range is designated in the sectional image of the standard sample, in the pore gray level acquisition unit, the representative regions of illustrating the pores are pointed out through a computer mouse within the given range given and the gravy level values of the corresponding regions are read, so that the gray level values can be obtained primarily.

Here, the gray-level values of representing the pores can be different from each other according to the arrangement of the peripheral particles. Accordingly, the gray level values of representing the pores are any range value, not singular value.

Figure 7:
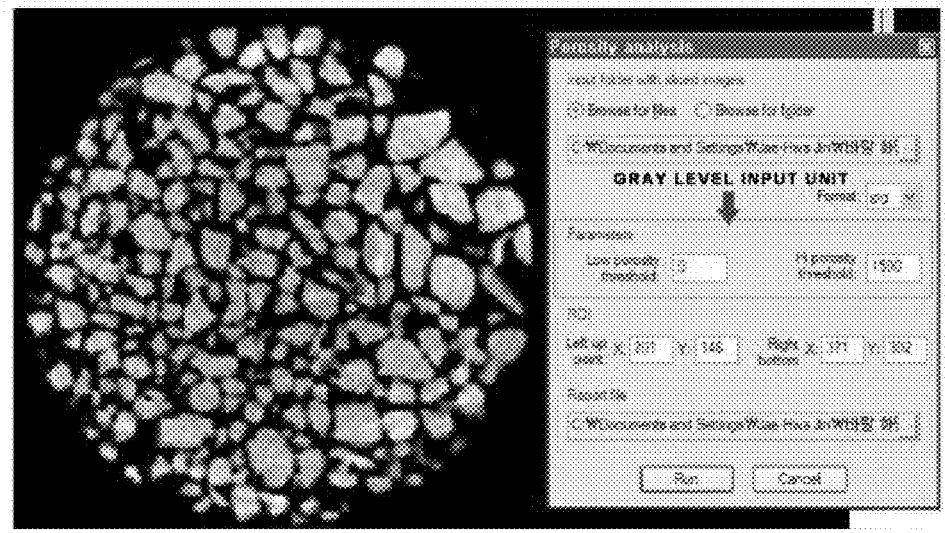
FIG. 7 is an example view illustrating a status of inputting a gray level range to a calculation input unit for utilizing the gray level range in the pore measurement of the measurement sample after the gray level range of representing the pore is obtained from the sectional image of the standard sample by means of a system for measuring a sample pore using a computed tomography (CT) and a standard sample according to one embodiment of the present invention.

FIG. 7 is an example view illustrating a status of inputting a gray level range to a calculation input unit for utilizing the gray level range in the pore measurement of the measurement sample after the gray level range of representing the pore is obtained from the sectional image of the standard sample of a system for measuring a sample pore using a computed tomography (CT) and a standard sample according to one embodiment of the present invention.

Figure 8:
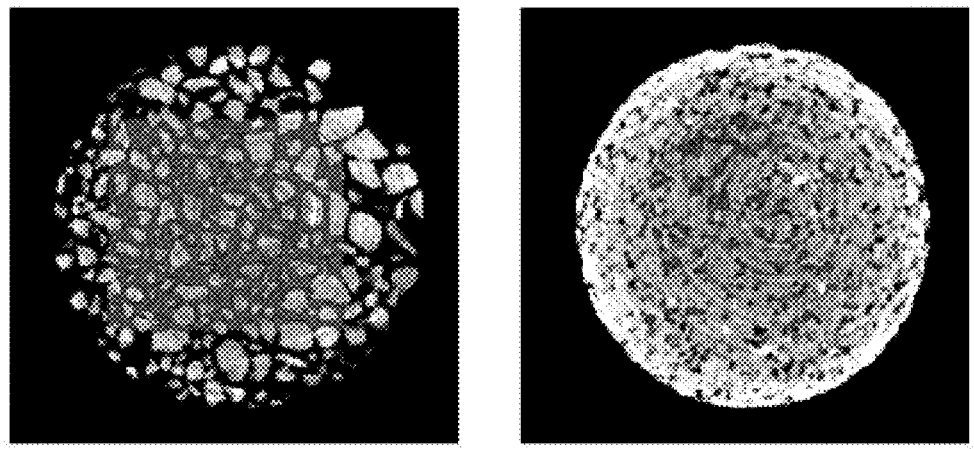
FIG. 8 is an example view illustrating colored pores identified from the sectional image through a count range acquisition unit and a pore gray level range acquisition unit by means of a system for measuring a sample pore using a computed tomography (CT) and a standard sample according to one embodiment of the present invention.

FIG. 8 is an example view illustrating colored pores identified from the sectional image through a count range acquisition unit and a pore gray level range acquisition unit of a system for measuring a sample pore using a computed tomography (CT) and a standard sample according to one embodiment of the present invention.

As shown in FIG. 7, if a gray level is inputted though a gray level input unit, a gray level range is acquired in a pore gray level range acquisition unit. The number of pixels corresponding to the gray level range is counted in a unit for counting the number of pore pixels. Accordingly, in a porosity calculation unit, the porosity is calculated as the ratio of the number of the recognized pore pixels, as compared with the number of the total pixels within the range of the designated count.

Through the above process, firstly, the porosity of the standard sample can be calculated. As shown in the left portion of FIG. 8, the pore portion is identified and colored by means of the gray level range designated already on the sectional image of the standard sample.

Since the techniques of coloring the corresponding portion are known to those skilled in the art, a detailed description on those is omitted here.

In other words, all colored portion of the pixels is counted and then, it finds the ratio of the number of the counted pixels as compared with the number of the entire pixels, so that the porosity thereof can be found in the corresponding sectional image.

Figure 9:
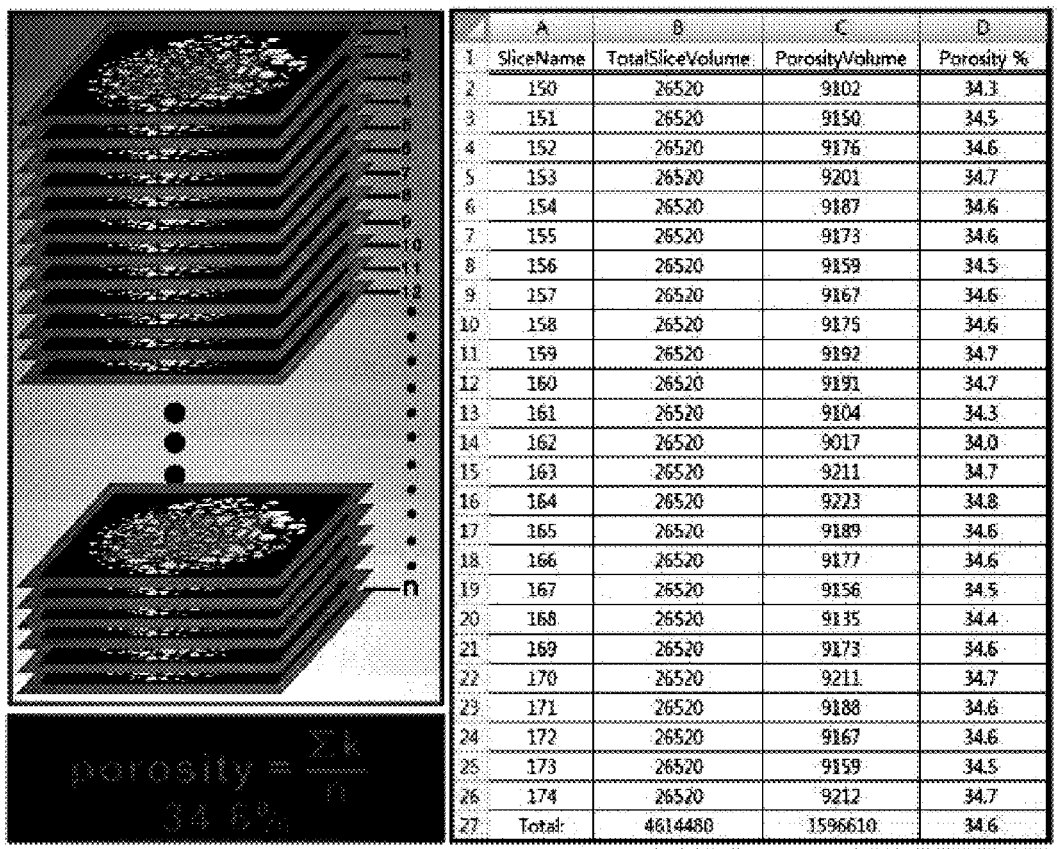
FIG. 9 is an example view illustrating a process of calculating a porosity through the calculation of the number of pixels corresponding to pores in each sectional image by applying an pore identification manner of any one sectional image to the adjacent sectional images all together by means of a system for measuring a sample pore using a computed tomography (CT) and a standard sample according to one embodiment of the present invention.

FIG. 9 is an example view illustrating a process of calculating a porosity through the calculation of the number of pixels corresponding to pores in each sectional image by applying an pore identification manner of any one sectional image to the adjacent sectional images all together by means of a system for measuring a sample pore using a computed tomography (CT) and a standard sample according to one embodiment of the present invention.

As shown in FIG. 9, the same manner is applied to the contiguous sectional images, so that it can find the porosity thereof within the range of the predetermined volume.

If the intervals of the adjacent cross-sectional images are infinitely narrow, the porosity can be derived very accurately.

It is essentially necessary to compare the derived porosity with the value of the porosity of the standard sample, which is already known through other mensurations.

Here, if it is a significant difference between the newly derived porosity and the pre-stored porosity, since there is an error in the initial gray level range, the ranges of the gray level thereof are enlarged or reduced to recalculate the porosity, thereby deriving the range of the gray level within the error range of two porosities.

As described above, when the gray level range of representing the pore is derived accurately in the standard sample, the corresponding gray level range is directly applied to the gray level range of representing the pore in the sectional image of the measurement sample and then, the rest computation processes are performed in the same manner as in the standard sample, so that it can find the porosity of the measurement sample exactly.

FIG. 9 is a diagram showing the number of total pixels within the count range by the sectional image, the number of pixels corresponding to the pore within the corresponding count range, and the results of calculating the porosities. Also, a formula for calculating the total porosity of the sectional images is illustrated at the lower portion thereof.

In other words, the central control unit serves to calculate a total porosity (in this case, 34.6%) by acquiring the porosities calculated on each cross-sectional image.

Figure 10:
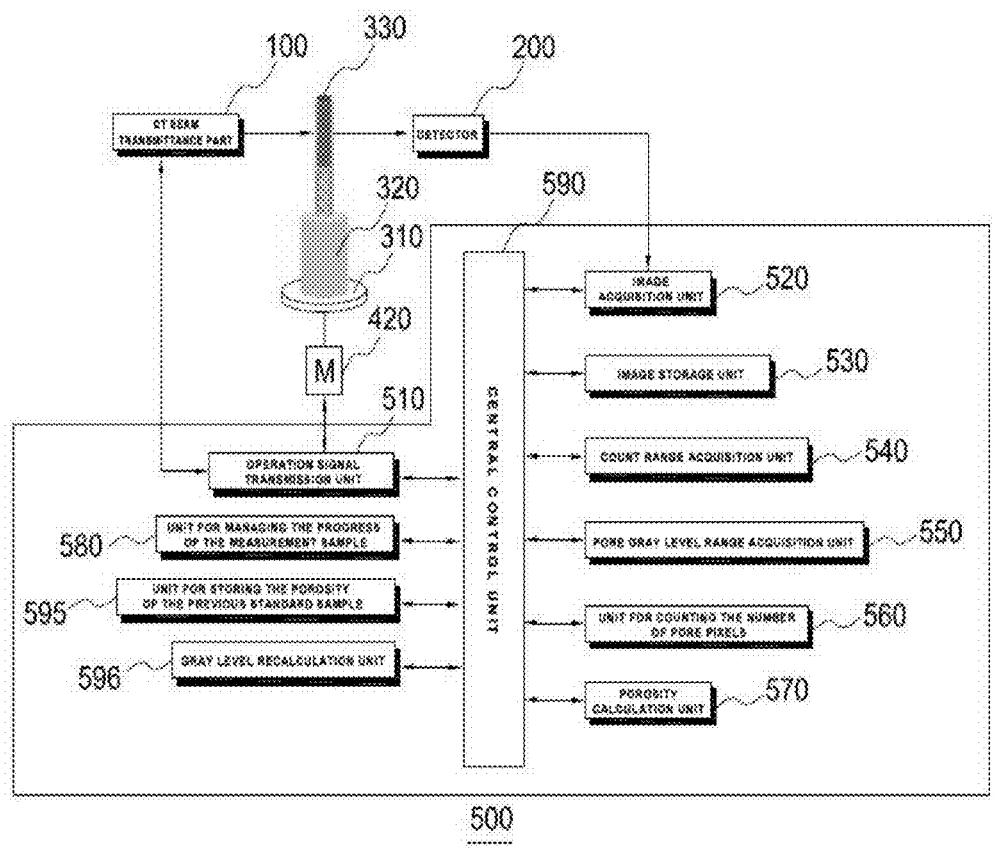
FIG. 10 is a block diagram illustrating a system for measuring a sample pore using a computed tomography (CT) and a standard sample according to one embodiment of the present invention.

FIG. 10 is a block diagram illustrating a system for measuring a sample pore using a computed tomography (CT) and a standard sample according to one embodiment of the present invention.

As shown in FIG. 10, the central control means 500 serves to transmit operation signals to the sample rotating motor 420, transmit a CT beam transmission signal to the CT beam transmission unit, acquire the sectional images of the standard sample and the measurement sample analyzed by the detector 200, acquire the count range and the gray level range of the pore from the sectional image of the standard sample, and calculate the number of pixels in the count range of the cross-sectional image of the measurement sample and the number of pixels corresponding to the gray level range of the pore with reference to the count range utilized in the cross-sectional image of the standard sample and the gray level range of the corresponding pore so as to measure the porosity of the measurement sample.

In order to perform the above operations, the central control means 500 includes:

an operation signal transmission unit 510 for transmitting the operation signals to the sample rotating motor 420 and transmitting the CT beam transmission signal to the CT beam transmission unit;

an image acquisition unit 520 for acquiring the sectional images of the standard sample and the measurement sample analyzed by the detector 200;

an image storage unit 530 for storing the sectional images acquired by the image acquisition unit 520;

a count range acquisition unit 540 for acquiring the count range so as to measure the pores of the standard sample and the measurement sample;

a pore gray level range acquisition unit 550 for acquiring the pore gray level range of a specific portion in the sectional images of the standard sample and the measurement sample;

an unit 560 for counting the number of pore pixels for receiving the count range acquired by the count range acquisition unit 540 and the pore gray level range acquired by the pore gray level range acquisition unit 550 and counting the number of pixels corresponding to the pore gray level range within the count range of the sectional images of the standard sample and the measurement sample;

a porosity calculation unit 570 for calculating the porosity with reference to the number of pixels corresponding to the pore gray level range counted by the unit 560 for counting the number of pore pixels and the number of the pixels within the count range;

an unit 580 for managing the progress of the measurement sample for receiving the count range acquired through the count range acquisition unit 540 and the pore gray level range acquired through the pore gray level range acquisition unit 550 so as to calculate the porosity from the sectional images of the standard sample acquired by the image acquisition unit 520, again transmitting the acquired count range and pore gray level range to the count range acquisition unit 540 and the pore gray level range acquisition unit 550 so as to calculate the porosity from the sectional images of the measurement sample acquired by the image acquisition unit 520, and again transmitting the counted number of the pixels to the porosity calculation unit 570 by transmitting the count signal to the unit 560 for counting the number of pore pixels so as to count the number of the pixels, thereby calculating the porosity thereof; and the central control unit 590 for controlling a signal flow between each unit.

The operation signal transmission unit 510 serves to transmit the operation signals to the sample rotating motor 420 and transmit the CT beam transmission signal to the CT beam transmission unit.

That is, if the user operates the program installed and constructed on the system so as to drive the system of the present invention, the central control unit 590 receives the operation signals and then, transmits them to the operation signal transmission unit 510.

Then, the operation signal transmission unit 510 transmits the operation signals to the sample rotating motor 420 to rotate the sample. Also, the operation signal transmission unit 510 transmits the CT beam transmission signal to the CT beam transmission unit, so that the CT beam is transmitted to the corresponding sample.

At this time, in the image acquisition unit 520, the sectional images of the standard sample and the measurement sample analyzed by the detector 200 are acquired.

Since the technology and the operation process for treating the data of the detector are already well-known to those skilled in the art, a detailed description is omitted here.

The sectional images acquired by the image acquisition unit 520 are any images shown in FIG. 9.

The sectional images acquired by the image acquisition unit 520 are stored in the image storage unit 530 according to the control of the central control unit 590.

The sectional images acquired by the image acquisition unit 520 stored in the image storage unit 530 are outputted to a monitor of the user so as to designate the count range by means of the user. A computer program capable of designating the count range is installed thereon to be displayed on the monitor.

Where the corresponding sectional image for designating the count range is outputted to the monitor, the user designates the left upper end point and the right lower end point as shown in FIG. 5. Accordingly, the count range acquisition unit 540 acquires the count range thereof.

As shown in FIG. 5, it can identify the designated range from the real photographs.

After the user designates the count range, the pore gray level range within the sectional images is designated. At this time, the user observes the gray level pixels and then, designates the gray level region.

For example, if the gray level of the standard sample for measuring the pore is designated in the range of 0 to 1,500, the central control unit is judged that the gray level of exceeding the range of 1,500 is any object other than the pore.

At this time, in the pore gray level range acquisition unit 550, the pore gray level range of the designated specific portion is acquired.

Concretely, the sectional images existed within the count range are outputted to the monitor of the user so as to designate the gray level through a computer program.

When the user designates the gray level on the monitor, the pore gray level range acquisition unit 550 acquires the pore gray level range.

The unit 560 for counting the number of pore pixels serves to receive the count range acquired by the count range acquisition unit 540 and the pore gray level range acquired by the pore gray level range acquisition unit 550 according to the control of the central control unit 590 and count the number of pixels corresponding to the pore gray level range within the count range of the sectional images of the standard sample and the measurement sample.

That is, as shown in FIG. 9, in case of the cross-sectional image #150, the number X of pixels within the count range is 26,520 according to the calculation of the central control unit and the number Y of pixels of the pores is 9,102 according to the calculation of the unit 560 for counting the number of pore pixels.

At this time, in the porosity calculation unit 570, the porosity (34.3%, $Z=(Y/X)*100\%$) of the corresponding sectional image is calculated.

As shown in FIG. 9, the number X of the total pixels within the count range of the total sectional images is 4,614,480 and the number Y of the total pixels of the pores within the range thereof is 1,596,610 according to the calculation of the unit 560 for counting the number of pore pixels. Also, it can be seen that the porosity ($Z=(Y/X)*100\%$) is 34.3%.

The above process illustrates an example of measuring the standard sample.

In the unit 580 for managing the progress of the measurement sample, the count range acquired through the count range acquisition unit 540 and the pore gray level range acquired through the pore gray level range acquisition unit 550 are received so as to calculate the porosity from the sectional images of the standard sample acquired by the image acquisition unit 520.

Here, the porosity of the samples should be calculated under the same conditions as described above so as to accurately measure the porosity of the measurement sample.

Thereafter, in the unit 580 for managing the progress of the measurement sample, the acquired count range and pore gray level range are again transmitted to the count range acquisition unit 540 and the pore gray level range acquisition unit 550 so as to calculate the porosity from the sectional images of the measurement sample acquired by the image acquisition unit 520, thereby acquiring the count range and the pore gray level range. Then, the counted number of the pixels is again transmitted to the porosity calculation unit 570 by transmitting the count signal to the unit 560 for counting the number of pore pixels so as to count the number of the pixels, thereby calculating the porosity thereof.

Since the calculation of the porosity of the measurement sample is identical with that of the standard sample, further description on this is omitted here.

In the meantime, a central control means 500 according to another embodiment of the present invention further includes:

an unit 595 for storing a porosity of a previous standard sample for storing a pore gray level range and a porosity of the standard sample calculated in advance; and a gray level recalculation unit 596 for generating a recalculation signal so as to recalculate the pore gray level range where the difference between the porosity of the standard sample calculated by the porosity calculation unit 570 and the porosity of the standard sample pre-stored in the unit 595 for storing the porosity of the previous standard sample is not within the error range thereof.

That is, in the unit 595 for storing the porosity of the previous standard sample, the pore gray level range and the porosity of the standard sample, which are calculated in advance through the immersion process, the gas process, and the mercury process, are stored.

The gray level recalculation unit 596 serves to generate the recalculation signal so as to recalculate the pore gray level range where the difference between the porosity of the standard sample calculated by the porosity calculation unit 570 and the porosity of the standard sample pre-stored in the unit 595 for storing the porosity of the previous standard sample is not within the error range thereof.

That is, the error range information is stored in a separated storage unit (not shown). At this time, if the difference between the porosity of the standard sample calculated by the porosity calculation unit 570 and the porosity of the standard sample pre-stored in the unit 595 for storing the porosity of the previous standard sample is not within the error range through an analysis of the central control unit (that is, if it exceeds the error range), in order to recalculate the pore gray level range by means of the user, the central control unit transmits an operation order signal to the gray level recalculation unit 596 and then, the gray level recalculation unit 596 generates the recalculation signal to be transmitted on the monitor of the user.

Thereafter, the user recalculates the pore gray level range again and then, recalculates the porosity thereof again.

Here, if the porosity of exceeding the error range is calculated, since the first gray level is wrongly designated, it is impossible to accurately calculate the porosity.

Figure 11:
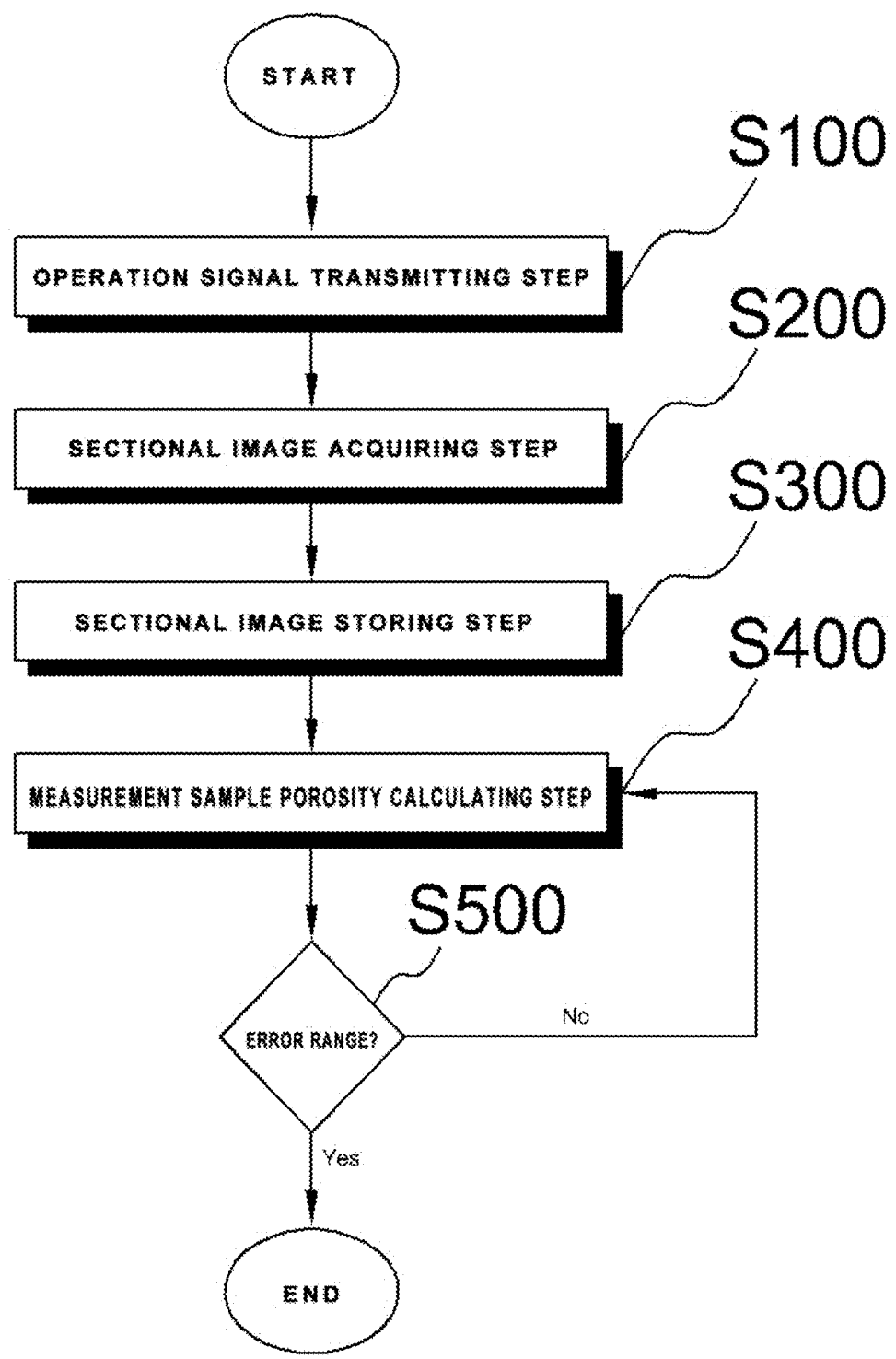
FIG. 11 is a flow chart illustrating a method for measuring a sample pore using a computed tomography (CT) and a standard sample according to one embodiment of the present invention.

FIG. 11 is a flow chart illustrating a method for measuring a sample pore using a computed tomography (CT) and a standard sample according to one embodiment of the present invention.

As shown in FIG. 11, a method for measuring a sample pore using a computed tomography (CT) and a standard sample according to one embodiment of the present invention includes:

an operation signal transmitting step S100 of transmitting operation signals to a sample rotating motor 420 by means of an operation signal transmission unit 510 to rotate a sample rotating device 310 and transmitting a CT beam transmission signal to a CT beam transmission unit;

a sectional image acquiring step S200 of acquiring sectional images of a standard sample and a measurement sample analyzed by a detector 200 by means of an image acquisition unit 520;

a sectional image storing step S300 of storing the sectional images acquired by the image acquisition unit 520 in an image storage unit 530; and a measurement sample porosity calculating step S400 of acquiring a count range and a gray level range of a pore from the sectional images of the standard sample, which are stored in the image storage unit 530, by means of a central control means and calculating the number of pixels in the count range of the sectional image of the measurement sample and the number of pixels corresponding to the gray level range of the pore with reference to the count range of the sectional images and the gray level range of the corresponding pore by means of the central control means so as to measure the porosity of the measurement sample.

That is, it transmits the operation signals to the sample rotating motor 420 by means of the operation signal transmission unit 510 to rotate the sample rotating device 310 and transmits the CT beam transmission signal to the CT beam transmission unit (S100).

Thereafter, in the image acquisition unit, it acquires the sectional images of the standard sample and the measurement sample analyzed by the detector 200 according to the control of the central control unit (S200).

Then, the sectional images acquired by the image acquisition unit 520 are stored in the image storage unit 530 according to the control of the central control unit (S300).

Continuously, after the count range and the gray level range of the pore from the sectional images of the standard sample stored in the image storage unit 530 are acquired in the central control means, it calculates the number of pixels in the count range of the sectional image of the measurement sample and the number of pixels corresponding to the gray level range of the pore with reference to the count range of the sectional images and the gray level range of the corresponding pore by means of the central control means, thereby measuring the porosity of the measurement sample (S400).

In the meantime, in a method for measuring a sample pore using a computed tomography (CT) and a standard sample according to another embodiment of the present invention, where the difference between the porosity of the standard sample calculated by the central control means and the porosity of the standard sample pre-stored in an unit 595 for storing the porosity of the previous standard sample is not within the error range thereof, a gray level recalculating step S500 of generating a recalculation signal so as to recalculate the pore gray level range in the central control means is performed next to the measurement sample porosity calculating step S400.

That is, when it corresponds to the error range thereof, the process of calculating the porosity of the measurement sample is performed. On the other hand, when it does not correspond to the error range thereof, it notifies the user so as to recalculate the pore gray level range.

Figure 12:
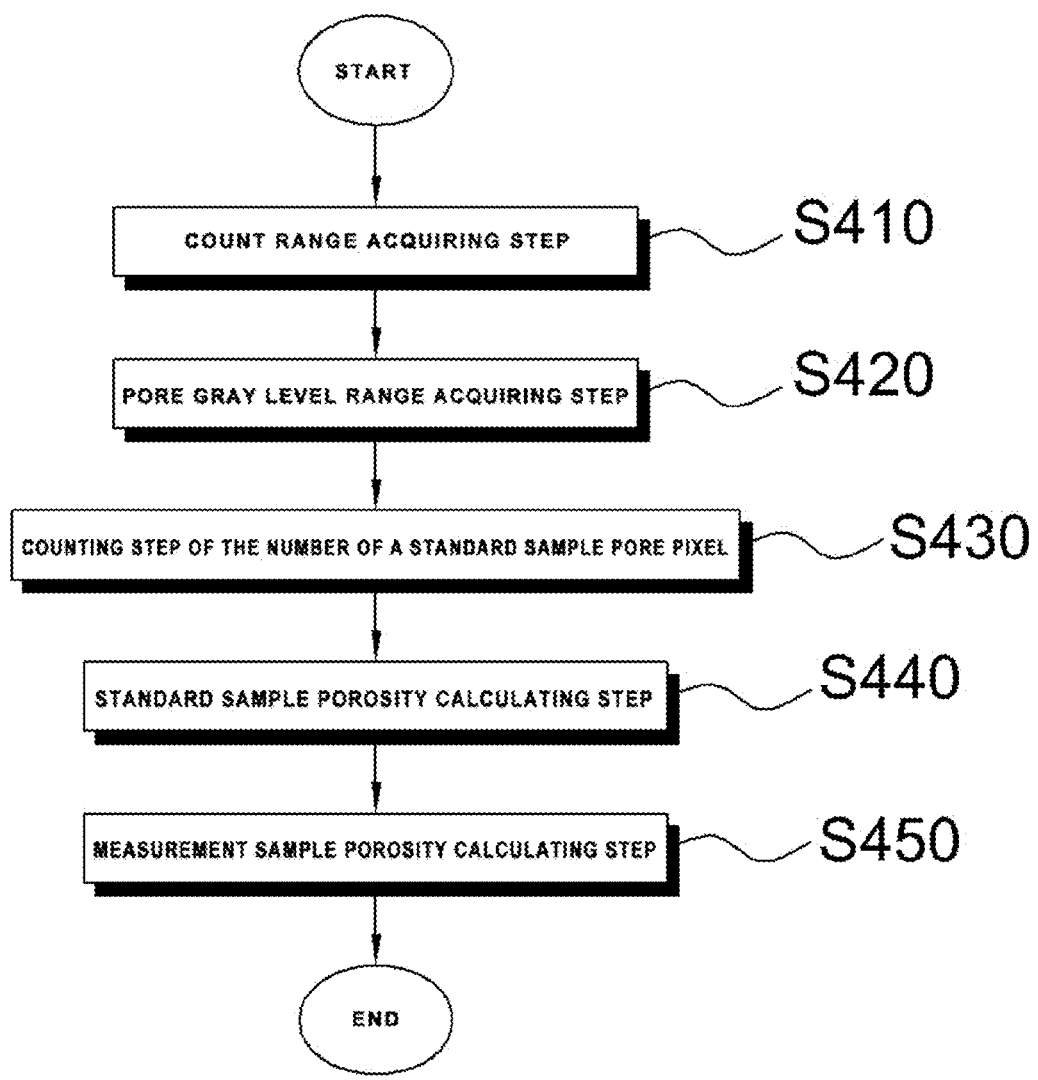
FIG. 12 is a flow chart illustrating a measurement sample porosity calculating step of a method for measuring a sample pore using a computed tomography (CT) and a standard sample according to one embodiment of the present invention.

FIG. 12 is a flow chart illustrating a measurement sample porosity calculating step of a method for measuring a sample pore using a computed tomography (CT) and a standard sample according to one embodiment of the present invention.

As shown in FIG. 12, the measurement sample porosity calculating step S400 includes:

a count range acquiring step 410 of acquiring the count range so as to measure the pores of the standard sample by means of a count range acquisition unit 540;

a pore gray level range acquiring step S420 of acquiring the pore gray level range of a specific portion in the sectional images of the standard sample by means of the pore gray level range acquisition unit 550;

a counting step S430 of the number of a standard sample pore pixel of receiving the count range acquired by the count range acquisition unit 540 and the pore gray level range acquired by the pore gray level range acquisition unit 550 in an unit 560 for counting the number of pore pixels and counting the number of pixels corresponding to the pore gray level range within the count range of the sectional images of the standard sample by means of the unit 560 for counting the number of pore pixels;

a standard sample porosity calculating step S440 of calculating the porosity of the standard sample with reference to the number of pixels corresponding to the pore gray level range counted by the unit 560 for counting the number of pore pixels and the number of the pixels within the count range by means of a porosity calculation unit 570; and a measurement sample porosity calculating step S450 of receiving the count range acquired through the count range acquisition unit 540 and the pore gray level range acquired through the pore gray level range acquisition unit 550 so as to calculate the porosity from the sectional images of the standard sample acquired by the image acquisition unit 520, again transmitting the acquired count range and pore gray level range to the count range acquisition unit 540 and the pore gray level range acquisition unit 550 so as to calculate the porosity from the sectional images of the measurement sample, and again transmitting the counted number of the pixels to the porosity calculation unit 570 by transmitting the count signal to the unit 560 for counting the number of pore pixels so as to count the number of the pixels, thereby calculating the porosity of the measurement sample by means of an unit 580 for managing the progress of the measurement sample.

That is, it acquires the count range designated by the user so as to measure the pores of the standard sample by means of the count range acquisition unit 540 (S410). Also, it acquires the pore gray level range of the specific portion designated by the user in the sectional images of the standard sample by means of the pore gray level range acquisition unit 550 (S420).

Then, it receives the count range acquired by the count range acquisition unit 540 and the pore gray level range acquired by the pore gray level range acquisition unit 550 in the unit 560 for counting the number of pore pixels and counts the number of pixels corresponding to the pore gray level range within the count range of the sectional images of the standard sample by means of the unit 560 for counting the number of pore pixels (S430).

Continuously, it calculates the porosity of the standard sample with reference to the number of pixels corresponding to the pore gray level range counted by the unit 560 for counting the number of pore pixels and the number of the pixels within the count range by means of a porosity calculation unit 570 (SS440).

After the above step, it can be determined whether it corresponds to the error range or not.

Thereafter, it receives the count range acquired through the count range acquisition unit 540 and the pore gray level range acquired through the pore gray level range acquisition unit 550 so as to calculate the porosity from the sectional images of the standard sample acquired by the image acquisition unit 520, again transmits the acquired count range and pore gray level range to the count range acquisition unit 540 and the pore gray level range acquisition unit 550 so as to calculate the porosity from the sectional images of the measurement sample, and again transmits the counted number of the pixels to the porosity calculation unit 570 by transmitting the count signal to the unit 560 for counting the number of pore pixels so as to count the number of the pixels, thereby finally calculating the porosity of the measurement sample by means of an unit 580 for managing the progress of the measurement sample (S450).

In the above step, the count range and the pore gray level range, which are the numerical data read from the cross-sectional images of the standard sample, can be utilized as it is, thereby remarkably enhance the accuracy and precision of the measurement of the porosity of the measurement sample.

According to the system for measuring the sample pore using the computed tomography (CT) and the standard sample and to the method thereof, there is an effect in that the sectional images on the standard sample and the measurement sample are acquired by using the computed tomography (CT) and the gray level range of the pore is acquired from the sectional images of the standard sample, and then, the corresponding range can be applied to the measurement sample, thereby reliably measuring the porosity of the measurement sample.

Although several exemplary embodiments of the present invention have been described for illustrative purposes, those skilled in the art will appreciate that various modifications, additions and substitutions are possible, without departing from the scope and spirit of the invention as disclosed in the accompanying claims.

INDUSTRIAL APPLICABILITY

The present invention relates to a system for measuring a sample pore using a computed tomography (CT) and a standard sample and to a method thereof, wherein the number of pixels in the count range of a cross-sectional image of the measurement sample and the number of pixels corresponding to the gray level range of the pore are calculated with reference to the count range utilized in the cross-sectional image of the standard sample and the gray level range of the pore so as to accurately measure the porosity of the measurement sample after performing a CT scan of the standard sample and the measurement sample together using a CT scanner, whereby making good use of it in the field of the geological resource core analysis.

What is claimed is:

1. A method for measuring a sample pore using a computed tomography (CT) and a standard sample comprising:

an operation signal transmitting step S100 of transmitting operation signals to a sample rotating motor by means of an operation signal transmission unit to rotate a sample rotating device and transmitting a CT beam transmission signal to a CT beam transmission unit;

a sectional image acquiring step S200 of acquiring sectional images of a standard sample and a measurement sample analyzed by a detector by means of an image acquisition unit 520;

a sectional image storing step S300 of storing the sectional images acquired by the image acquisition unit in an image storage unit; and a measurement sample porosity calculating step S400 of acquiring a count range and a gray level range of a pore from the sectional images of the standard sample, which are stored in the image storage unit, by means of a central control means and calculating the number of pixels in the count range of the sectional image of the measurement sample and the number of pixels corresponding to the gray level range of the pore with reference to the count range of the sectional images and the gray level range of the corresponding pore by means of the central control means so as to measure the porosity of the measurement sample.

2. A method for measuring a sample pore using a computed tomography (CT) and a standard sample as claimed in claim 1, wherein the measurement sample porosity calculating step S400 comprises:

a count range acquiring step of acquiring the count range so as to measure the pores of the standard sample by means of a count range acquisition unit;

a pore gray level range acquiring step S420 of acquiring the pore gray level range of a specific portion in the sectional images of the standard sample by means of the pore gray level range acquisition unit;

a counting step S430 of the number of a standard sample pore pixel of receiving the count range acquired by the count range acquisition unit and the pore gray level range acquired by the pore gray level range acquisition unit in an unit for counting the number of pore pixels and counting the number of pixels corresponding to the pore gray level range within the count range of the sectional images of the standard sample by means of the unit for counting the number of pore pixels;

a standard sample porosity calculating step S440 of calculating the porosity of the standard sample with reference to the number of pixels corresponding to the pore gray level range counted by the unit for counting the number of pore pixels and the number of the pixels within the count range by means of a porosity calculation unit; and a measurement sample porosity calculating step S450 of receiving the count range acquired through the count range acquisition unit and the pore gray level range acquired through the pore gray level range acquisition unit so as to calculate the porosity from the sectional images of the standard sample acquired by the image acquisition unit, again transmitting the acquired count range and pore gray level range to the count range acquisition unit and the pore gray level range acquisition unit so as to calculate the porosity from the sectional images of the measurement sample, and again transmitting the counted number of the pixels to the porosity calculation unit by transmitting the count signal to the unit for counting the number of pore pixels so as to count the number of the pixels, thereby calculating the porosity of the measurement sample by means of an unit for managing the progress of the measurement sample.

3. A method for measuring a sample pore using a computed tomography (CT) and a standard sample as claimed in claim 1, wherein the central control means serves to calculate the number of pixels in the count range, calculate the number of pixels corresponding to the gray level range, and calculate the porosities per each sectional image with reference to the calculated number of pixels.

4. A method for measuring a sample pore using a computed tomography (CT) and a standard sample as claimed in claim 1, wherein the ingredients of the standard sample are identical with those of the measurement sample.

5. A method for measuring a sample pore using a computed tomography (CT) and a standard sample comprising:
    an operation signal transmitting step S100 of transmitting operation signals to a sample rotating motor by means of an operation signal transmission unit to rotate a sample rotating device and transmitting a CT beam transmission signal to a CT beam transmission unit;
    a sectional image acquiring step S200 of acquiring sectional images of a standard sample and a measurement sample analyzed by a detector by means of an image acquisition unit;
    a sectional image storing step S300 of storing the sectional images acquired by the image acquisition unit in an image storage unit;
    a measurement sample porosity calculating step S400 of acquiring a count range and a gray level range of a pore from the sectional images of the standard sample, which are stored in the image storage unit, by means of a central control means and calculating the number of pixels in the count range of the sectional image of the measurement sample and the number of pixels corresponding to the gray level range of the pore with reference to the count range of the sectional images and the gray level range of the corresponding pore by means of the central control means so as to measure the porosity of the measurement sample; and
    a gray level recalculating step S500 of generating a recalculation signal so as to recalculate the pore gray level range in the central control means, where the difference between the porosity of the standard sample calculated by the central control means and the porosity of the standard sample pre-stored in an unit for storing the porosity of the previous standard sample is not within the error range thereof.

6. A method for measuring a sample pore using a computed tomography (CT) and a standard sample as claimed in claim 5, wherein the porosity of the standard sample stored in the unit for storing the porosity of the previous standard sample is calculated in advance through an immersion process, a gas process, and a mercury process.

7. A method for measuring a sample pore using a computed tomography (CT) and a standard sample as claimed in claim 5, wherein the measurement sample porosity calculating step S400 comprises:
    a count range acquiring step of acquiring the count range so as to measure the pores of the standard sample by means of a count range acquisition unit;
    a pore gray level range acquiring step S420 of acquiring the pore gray level range of a specific portion in the sectional images of the standard sample by means of the pore gray level range acquisition unit;
    a counting step S430 of the number of a standard sample pore pixel of receiving the count range acquired by the count range acquisition unit and the pore gray level range acquired by the pore gray level range acquisition unit in an unit for counting the number of pore pixels and counting the number of pixels corresponding to the pore gray level range within the count range of the sectional images of the standard sample by means of the unit for counting the number of pore pixels;
    a standard sample porosity calculating step S440 of calculating the porosity of the standard sample with reference to the number of pixels corresponding to the pore gray level range counted by the unit for counting the number of pore pixels and the number of the pixels within the count range by means of a porosity calculation unit; and
    a measurement sample porosity calculating step S450 of receiving the count range acquired through the count range acquisition unit and the pore gray level range acquired through the pore gray level range acquisition unit so as to calculate the porosity from the sectional images of the standard sample acquired by the image acquisition unit, again transmitting the acquired count range and pore gray level range to the count range acquisition unit and the pore gray level range acquisition unit so as to calculate the porosity from the sectional images of the measurement sample, and again transmitting the counted number of the pixels to the porosity calculation unit by transmitting the count signal to the unit for counting the number of pore pixels so as to count the number of the pixels, thereby calculating the porosity of the measurement sample by means of an unit for managing the progress of the measurement sample.

8. A method for measuring a sample pore using a computed tomography (CT) and a standard sample as claimed in claim 5, wherein the central control means serves to calculate the number of pixels in the count range, calculate the number of pixels corresponding to the gray level range, and calculate the porosities per each sectional image with reference to the calculated number of pixels.

9. A method for measuring a sample pore using a computed tomography (CT) and a standard sample as claimed in claim 5, wherein the ingredients of the standard sample are identical with those of the measurement sample.

* * * * *